(12) United States Patent
Kamada et al.

(10) Patent No.: US 9,890,326 B2
(45) Date of Patent: Feb. 13, 2018

(54) LIGHT UP-CONVERSION LUMINESCENT SUBSTANCE

(71) Applicant: National Institute of Advanced Industrial Science and Technology, Tokyo (JP)

(72) Inventors: Kenji Kamada, Osaka (JP); Kenji Kobayashi, Shizuoka (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 135 days.

(21) Appl. No.: 14/773,037

(22) PCT Filed: Feb. 25, 2014

(86) PCT No.: PCT/JP2014/054546
§ 371 (c)(1),
(2) Date: Nov. 5, 2015

(87) PCT Pub. No.: WO2014/136619
PCT Pub. Date: Sep. 12, 2014

(65) Prior Publication Data
US 2016/0053168 A1  Feb. 25, 2016

(30) Foreign Application Priority Data
Mar. 5, 2013 (JP) ................. 2013-043145

(51) Int. Cl.
*C09K 11/06* (2006.01)
*C07D 321/00* (2006.01)
*C07D 493/08* (2006.01)
*H05B 33/14* (2006.01)
*H01L 51/00* (2006.01)

(52) U.S. Cl.
CPC ............ *C09K 11/06* (2013.01); *C07D 321/00* (2013.01); *C07D 493/08* (2013.01); *H05B 33/14* (2013.01); *C09K 2211/1011* (2013.01); *H01L 51/0052* (2013.01); *H01L 51/0087* (2013.01)

(58) Field of Classification Search
CPC ................. C09K 11/06; C09K 2211/1011
See application file for complete search history.

(56) References Cited

U.S. PATENT DOCUMENTS

| 5,912,257 A * | 6/1999 | Prasad ................. A61K 41/008 250/338.1 |
| 2008/0103279 A1 | 5/2008 | Heun et al. |
| 2008/0171225 A1 | 7/2008 | Stoessel et al. |
| 2010/0301285 A1 | 12/2010 | Miteva et al. |
| 2011/0013263 A1 | 1/2011 | Miteva et al. |

FOREIGN PATENT DOCUMENTS

| JP | 2008-506798 | 3/2008 |
| JP | 2008-538350 | 10/2008 |
| JP | 2011-505479 | 2/2011 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Ceroni, Chemistry A European Journal, Energy Up-Conversion by Low-Power Excitation: New Applications of an Old Concept, 2011, 17, pp. 9560-9564.*
Fujiwara et al, The Journal of Organic Chemistry, Double Alkylene-Strapped Diphenylanthracene as a Photostable and Intense Solid-State Blue-Emitting Material, 2013, 78, pp. 2206-2212.*
International Search Report, PCT/JP2014/054546, dated May 27, 2014.
P. Ceroni, "Energy Up-Conversion by Low-Power Excitation: New Applications of an Old Concept," Chem. Eur. J. 2011, 17, 9560-9564.
Y. Fujwara, et al., "Double Alkylene-Strapped Diphenylanthracene as a Photostable and Intense Solid-State Blue-Emitting Material," J. Org. Chem., Jan. 16, 2013, vol. 78(6), pp. 2206-2212.
T. Trupke, et al., "Efficiency Enhancement of Solar Cells by Luminescent Up—Conversion of Sunlight," Solar Energy Materials and Solar Cells, Nov. 2006, vol. 90, pp. 3327-3338.

* cited by examiner

*Primary Examiner* — Paul A Zucker
(74) *Attorney, Agent, or Firm* — McDonald Hopkins LLC

(57) ABSTRACT

To provide a novel light up-conversion organic luminescent substance having a high light up-conversion efficiency. A light up-conversion luminescent substance which comprises a compound represented by general formula (1).

3 Claims, 1 Drawing Sheet

LIGHT UP-CONVERSION LUMINESCENT SUBSTANCE

TECHNICAL FIELD

The present invention relates to a light up-conversion luminescent substance that converts long-wavelength light to short-wavelength light, and a light up-conversion material containing the same.

BACKGROUND ART

In the related art, light up-conversion luminescent substances that convert long-wavelength light to short-wavelength light are known. The light up-conversion luminescent substances and inorganic light up-conversion luminescent substances in which a rare-earth element or the like is used are known. The inorganic light up-conversion luminescent substances have been applied, for example, to IR cards that convert infrared laser light to visible light, and have already been brought into practical use.

On the other hand, when inorganic light up-conversion luminescent substances in which an organic compound is used, it is known that an intense and broad absorption spectrum of the organic compound is used to enable light up-conversion with broader wavelengths and lower incident power compared with the inorganic light up-conversion luminescent substances. An example of application of the organic light up-conversion luminescent substances is organic solar cells. In an organic solar cell, those generating free charge carriers from solar light are ultraviolet light and blue light. Hence, it is expected that the photoelectric conversion efficiency of the organic solar cell will improve by using an organic light up-conversion luminescent substance in the organic solar cell to convert long-wavelength light such as green and red light into short-wavelength light such as blue light. Thus, the organic light up-conversion luminescent substances have received attention in recent years (see, e.g., Patent Document 1, Non-Patent Documents 1 and 2).

The organic light up-conversion luminescent substance is generally used together with a photosensitizer, and is used as an organic light up-conversion material. An example of a mechanism of light up-conversion in a currently known organic light up-conversion material includes the following mechanism. First, a photosensitizer molecule ($^1$A) in its ground state absorbs light energy to transit to an excited singlet state ($^1$A*) ($^1$A+hν→$^1$A*). Next, intersystem crossing to an excited triplet state ($^3$A*) rapidly occurs ($^1$A*→$^3$A*), and energy is transferred from the photosensitizer molecule in the excited triplet state to a luminescent molecule. As a result, the photosensitizer molecule loses the energy to return into its ground state. On the other hand, an luminescent molecule ($^1$E) in its ground state changes into an excited triplet ($^3$E*) (triplet-triplet energy transfer: $^3$A*+$^1$E→$^1$A+$^3$E*). When the concentration of luminescent molecules having changed into the excited triplet state increases, interaction between the luminescent molecules having changed into the excited triplet state occurs more efficiently, and energy transfers from the one luminescent molecule having changed into the excited triplet state to the other luminescent molecule. At this time, the one luminescent molecule having changed into the excited triplet state returns to the ground state, and the other changes into an excited singlet state (triplet-triplet annihilation process: $^3$E*+$^3$E*→$^1$E+$^1$E*). Then, up-converted light ($^1$E*→$^1$E+hν$_f$) is emitted as fluorescence from the luminescent molecule having changed into the excited singlet state. Such a mechanism is called "triplet-triplet annhilation up-conversion," "photochemical up-conversion," and so on.

Considering such a mechanism, in the organic light up-conversion material, it is necessary for the energy of the excited triplet state of the luminescent substance to be about half of the energy of the excited singlet state. For this reason, a luminescent substance with a molecule having an aromatic ring backbone may be used. Moreover, a photosensitizer with an organic metal complex that produces an excited triplet state with high efficiency may be used.

For example, a light up-conversion luminescent substance in a blue light emitting region, anthracene, 9,10-diphenyl anthracene and the like, are known. However, light up-conversion efficiency (i.e., conversion efficiency from long-wavelength light to short-wavelength light) using such a luminescent substance is as low as about 3 to 5%, and development of a novel organic light up-conversion material having higher light up-conversion efficiency is needed.

PRIOR ART DOCUMENTS

Patent Documents

Patent Document 1: Japanese Translation of PCT Application No. 2008-506798.

Non-Patent Document

Non-Patent Document 1: Ceroni, P. Energy up-conversion by low-power excitation: new applications of an old concept. Chemistry (Weinheim an der Bergstrasse, Germany) 2011, 17, 9560-4.

Non-Patent Document 2: Trupke, T.; Shalav, a.; Richards, B. S.; Wurfel, P.; Green, M. a. Efficiency enhancement of solar cells by luminescent up-conversion of sunlight. Solar Energy Materials and Solar Cells 2006, 90, 3327-3338.

SUMMARY

Problems to be Solved by the Invention

It is a primary objective of the present invention to provide a novel organic light up-conversion luminescent substance realizing high light up-conversion efficiency, and a light up-conversion material containing the same.

Means for Solving the Problem

The present inventors studied diligently to solve the above-described problem. As a result, it was found that a light up-conversion material having high light up-conversion efficiency can be obtained by using a compound represented by the below general formula (1) as a light up-conversion luminescent substance. The present invention was accomplished by further study based on such a finding.

That is, the present invention provides the following aspects.

Item 1. A light up-conversion luminescent substance comprising a compound represented by the following general formula (1):

[Chemical 1]

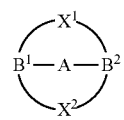

(1)

In general formula (1), group A represents a bivalent moiety of a polycyclic aromatic compound with 3 to 5 condensed rings optionally having a substituent.

Group $B^1$ and group $B^2$ each independently represent a trivalent group represented by the following general formula (2a) or (2b).

[Chemical 2]

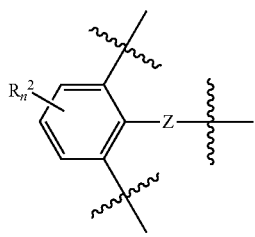

(2a)

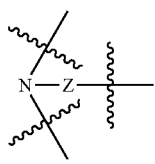

(2b)

In each of general formulas (2a) and (2b), group Z binds to group A, the remaining two binding hands respectively bind to group $X^1$ and group $X^2$, and group Z represents a single bond, or a saturated or unsaturated, straight-chain or branched-chain alkylene group. $R_n^2$ is 0 to 3 substituents which substitute for a hydrogen atom on a benzene ring and each independently represent an alkyl group, an alkoxy group, a phenyl group, a hydroxyl group, or an amino group.

Group $X^1$ and group $X^2$ each independently represent a straight-chain or branched-chain alkylene group with a carbon number of two or more, optionally having at least one bond selected from the group consisting of an ether bond, an ester bond, an amide bond and a sulfide bond.

Item 2. The light up-conversion luminescent substance according to Item 1, wherein in general formula (1), group A is any one of polycyclic aromatic compound moieties represented by the following general formulas (A1) to (A23)

[Chemical 3]

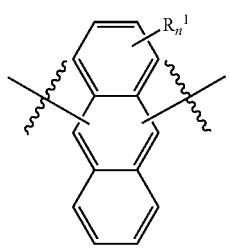

(A1)

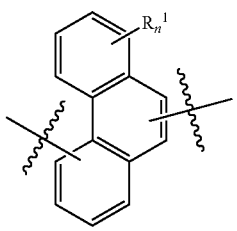

(A2)

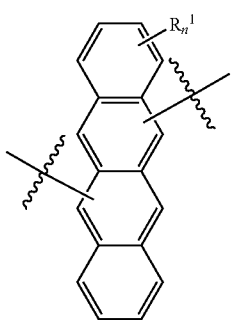

(A3)

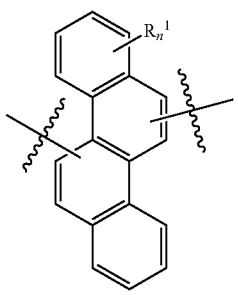

(A4)

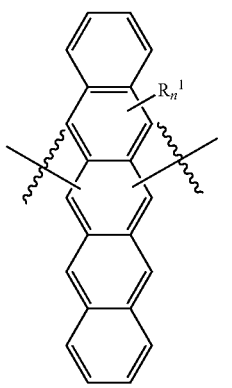

(A5)

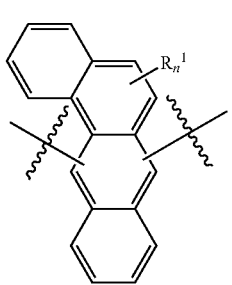

(A6)

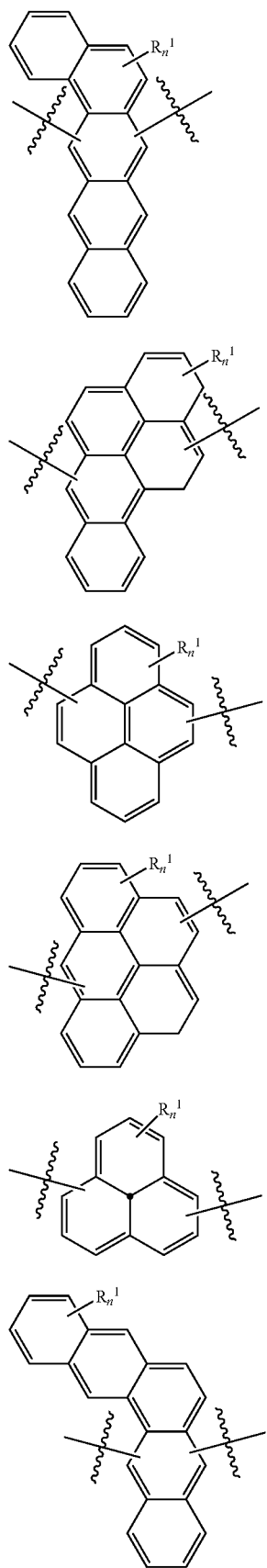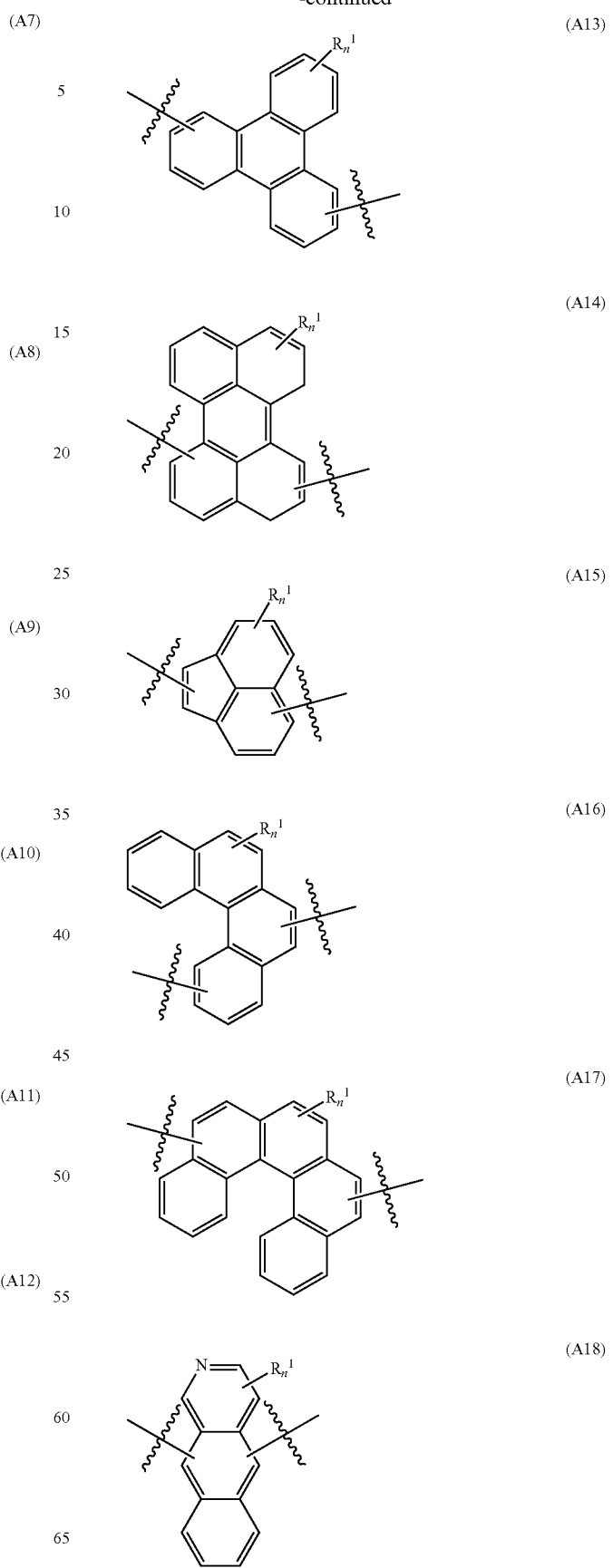

-continued

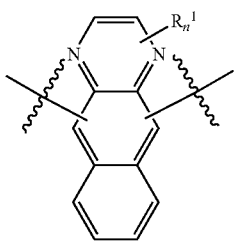
(A19)

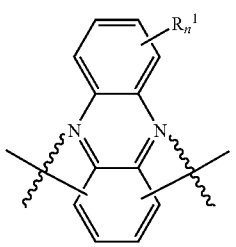
(A20)

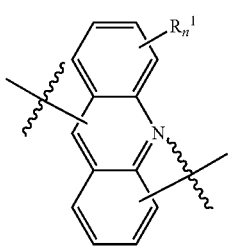
(A21)

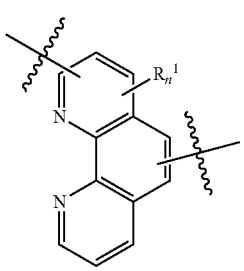
(A22)

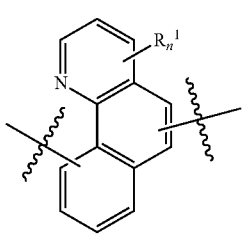
(A23)

In each of general formulas (A1) to (A23), bivalent binding hands each exist at any position substitutable with a hydrogen atom on an aromatic ring. $R_n^1$ is 0 or more substituents which each substitute for a hydrogen atom bound to an aromatic ring and each independently represent an alkyl group, an alkoxy group, a phenyl group, a hydroxyl group, or an amino group.

Item 3. The light up-conversion luminescent substance according to Item 1 or 2, wherein in general formula (1), group A is any one of polycyclic aromatic compound moieties represented by the following general formulas (A1-1), (A1-2), (A2-1), (A3-1), (A4-1), (A5-1), (A5-2), (A6-1), (A9-1), (A9-2), (A9-3), (A9-4), (A14-1), (A14-2), (A14-3), and (A14-4)

[Chemical 4]

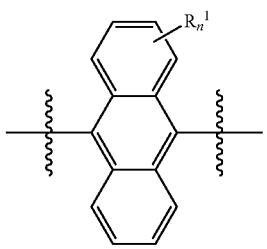
(A1-1)

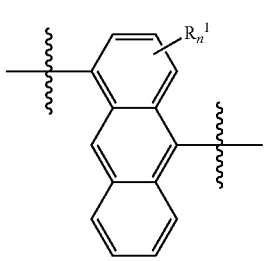
(A1-2)

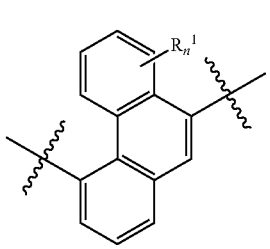
(A2-1)

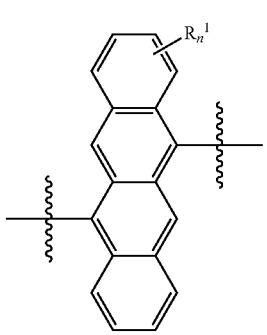
(A3-1)

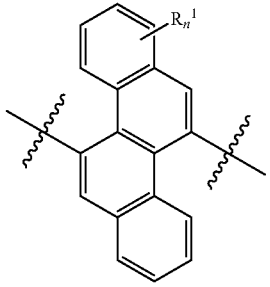
(A4-1)

(A5-1)
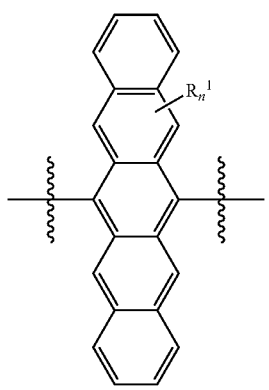
(A5-2)
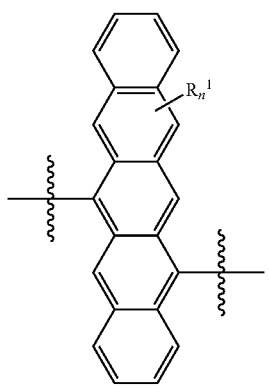
(A6-1)
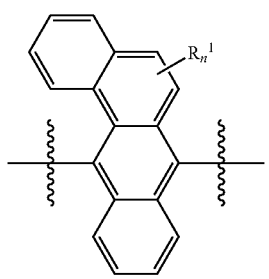
(A9-1)
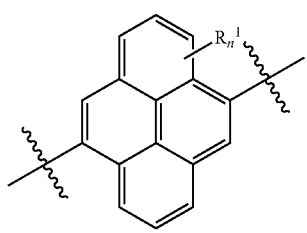
(A9-2)
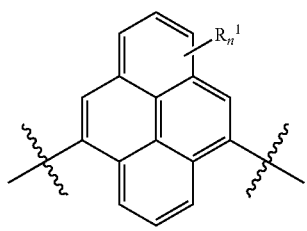
(A9-3)
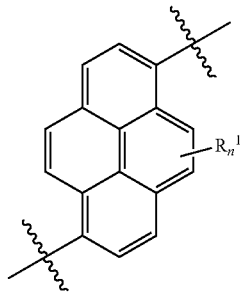
(A9-4)
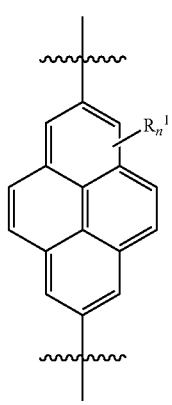
(A14-1)
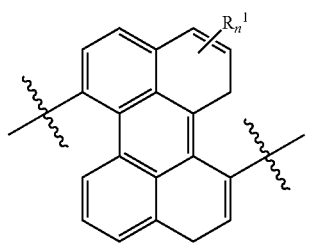
(A14-2)
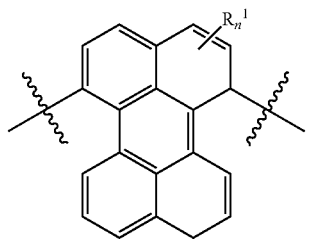
(A14-3)
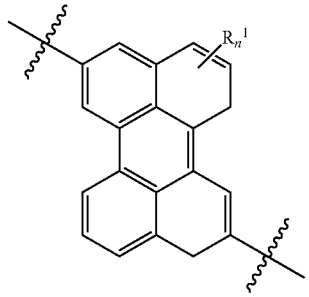

-continued (A14-4)

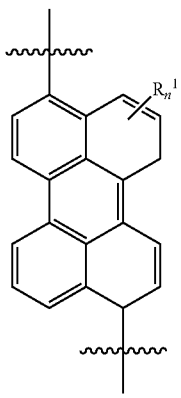

In each of general formulas (A1-1), (A1-2), (A2-1), (A3-1), (A4-1), (A5-1), (A5-2), (A6-1), (A9-1), (A9-2), (A9-3), (A9-4), (A14-1), (A14-2), (A14-3), and (A14-4), $R_n^1$ is similar to that in each of the above general formulas (A1) to (A23).

Item 4. The light up-conversion luminescent substance according to any one of Items 1 to 3, wherein group $B^1$ and group $B^2$ each independently represent any one of trivalent groups represented by the following general formulas (3a-1) to (3a-4)

[Chemical 5]

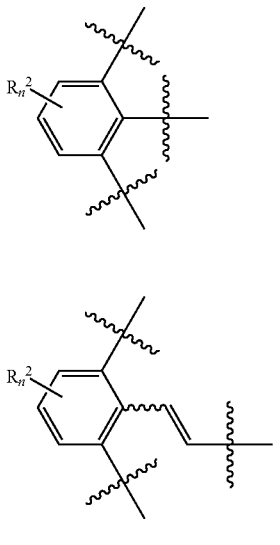

(3a-1)

(3a-2)

(3a-3)

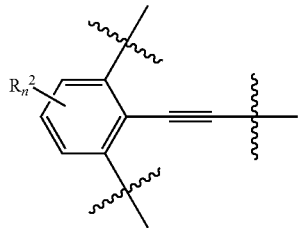

(3a-4)

In each of general formulas (3a-1) to (3a-4), $R_n^2$ is similar to that in general formula (2a).

Item 5. The light up-conversion luminescent substance according to any one of Items 1 to 4, wherein in general formula (1), group $X^1$ and group $X^2$ each independently represent a straight-chain alkylene group with a carbon number of 5 to 10, optionally having at least one bond selected from the group consisting of an ether bond, an ester bond, an amide bond, and a sulfide bond.

Item 6. A light up-conversion material comprising the light up-conversion luminescent substance according to any one of Items 1 to 5, and a photosensitizer.

Item 7. The light up-conversion material according to Item 6, further comprising a solvent, a resin, or a glass.

Item 8. A method of converting a light wavelength, including irradiating the light up-conversion material according to Item 6 or 7 with light to cause emission of light having a shorter wavelength than the radiating light.

Advantages of the Invention

According to the present invention, it is possible to provide a light up-conversion luminescent substance realizing high light up-conversion efficiency, and a light up-conversion material containing the same.

DETAILED DESCRIPTION OF THE INVENTION

Figure 1:
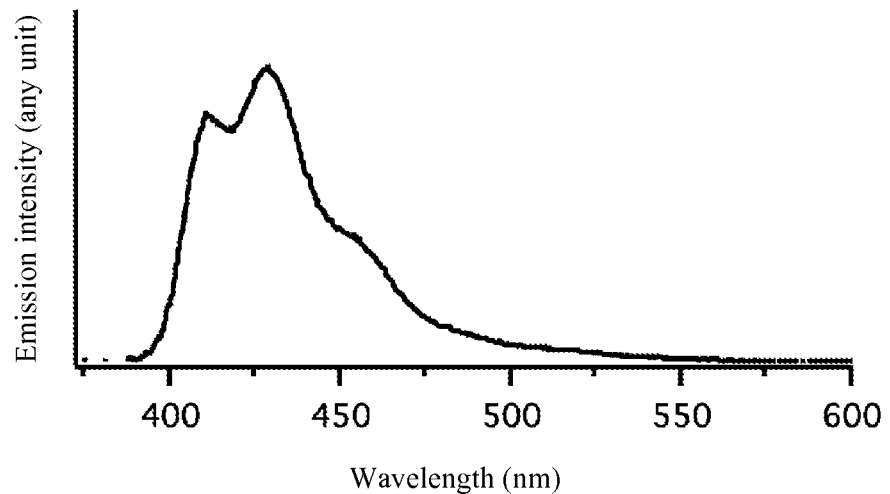
FIG. 1 is a graph showing a relation between a wavelength of emission and an emission intensity by a light up-conversion material obtained in Example 1.

A light up-conversion luminescent substance of the present invention has a feature of comprising a compound represented by the following general formula (1).

[Chemical 6]

(1)

In the present invention, the "light up-conversion luminescent substance" means a compound that emits light having a shorter wavelength than absorbed light. The light up-conversion luminescent substance of the present invention and a light up-conversion material containing the same will be described in detail.

Light Up-conversion Luminescent Substance

The light up-conversion luminescent substance is a compound represented by the above general formula (1), and has a function of emitting light having a shorter wavelength than light absorbed by the later-described light up-conversion material. In general formula (1), group A binds to group $B^1$ and group $B^2$. Moreover, group $B^1$, group $X^1$, group $B^2$, and group $X^2$ bind in this order to form a ring, and group A is positioned in this ring.

In general formula (1), group A represents a bivalent moiety of a polycyclic aromatic compound with 3 to 5 condensed rings optionally having a substituent. Examples of the aromatic ring constituting group A include a benzene ring, a cyclopentadienyl ring, a pyridine ring, a pyrazine ring, a pyrimidine ring, a pyridazine ring, a furan ring, a thiophene ring, and a silole ring.

Specific examples of group A include polycyclic aromatic compound moieties represented by the following general formulas (A1) to (A23).

[Chemical 7]

(A1)

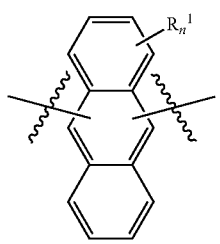

(A2)

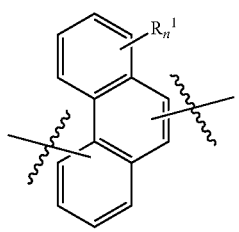

(A3)

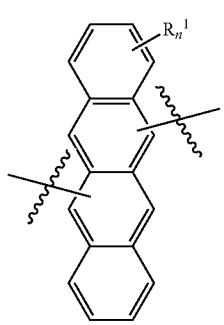

-continued (A4)

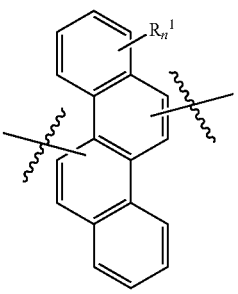

(A5)

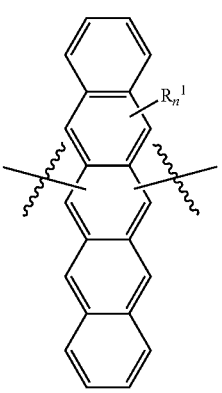

(A6)

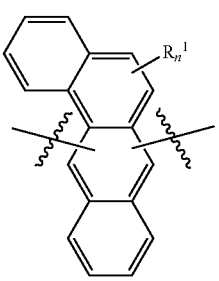

(A7)

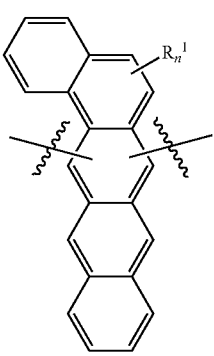

(A8)

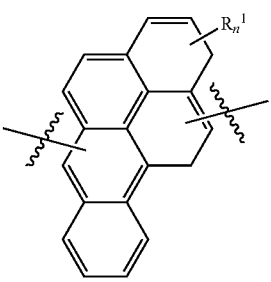

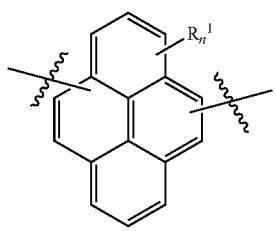 (A9)
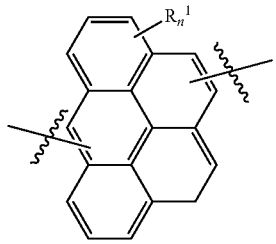 (A10)
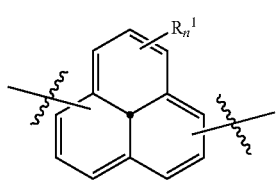 (A11)
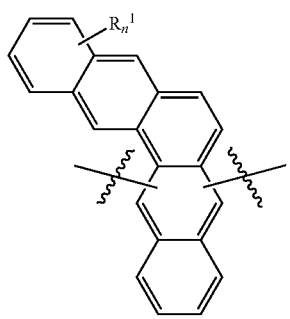 (A12)
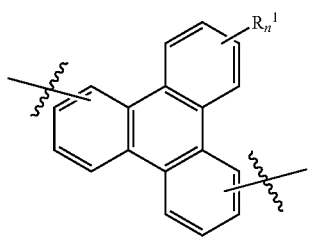 (A13)
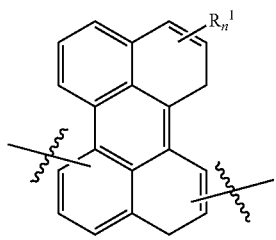 (A14)
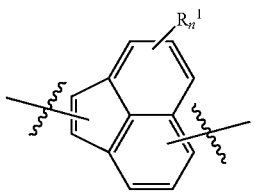 (A15)
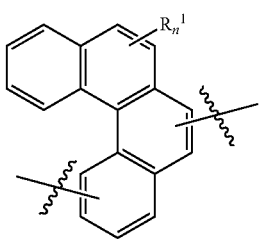 (A16)
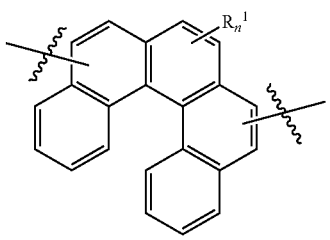 (A17)
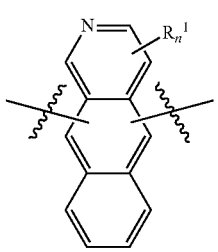 (A18)
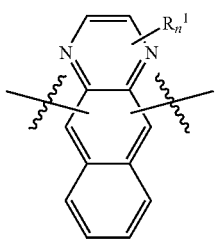 (A19)
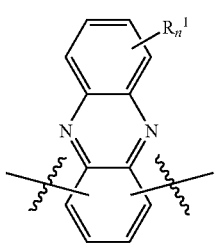 (A20)

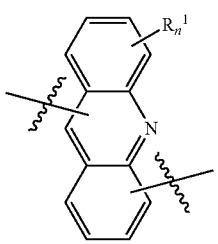
(A21)

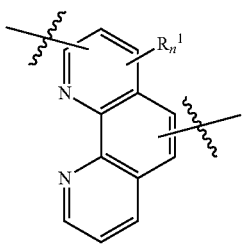
(A22)

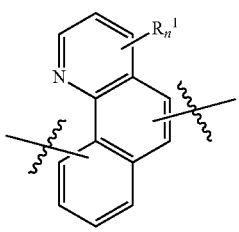
(A23)

In each of general formulas (A1) to (A23), positions of bivalent binding hands are not particularly limited, and the bivalent binding hands each exist at any position substitutable with a hydrogen atom on an aromatic ring. The bivalent binding hands preferably each exist on the same aromatic ring or on aromatic rings adjacent to each other. As a result, it can be considered that the size of the ring can be reduced, interaction between luminescent substances becomes likely occur, and it becomes possible to further improve the light up-conversion efficiency. Moreover, the bivalent binding hands preferably each exist at a position where a radical is likely to be generated when no binding hand exists. Existence of each binding hand at such a position inhibits generation of a radical at such a position, and suppresses any decrease in the light up-conversion efficiency due to formation of a dimer resulting from radical reaction between luminescent substances.

In each of general formulas (A1) to (A23), $R_n^1$ is zero or more substituents which each substitute for a hydrogen atom bound to an aromatic ring. Although an upper limit of the number of $R_n^1$ differs according to the number of hydrogen atoms bound to the aromatic ring in each of general formulas (A1) to (A23), the upper limit is typically about 0 to 8, preferably about 0 to 4. Zero or more $R_n^1$ each independently represent an alkyl group, an alkoxy group, a phenyl group, a hydroxyl group, or an amino group. When $R_n^1$ is an alkyl group or an alkoxy group, the carbon number is not particularly limited, but from the view point of reducing the steric hindrance of group A and facilitating interaction between luminescent substances, the carbon number includes preferably about 1 to 4.

In general formula (1), examples of preferred group A include polycyclic aromatic compound moieties represented by the following general formulas (A1-1), (A1-2), (A2-1), (A3-1), (A4-1), (A5-1), (A5-2), (A6-1), (A9-1), (A9-2), (A9-3), (A9-4), (A14-1), (A14-2), (A14-3), and (A14-4). As a result of such a structure of group A, the luminescent substance has a structure in which a ring formed by group $B^1$, group $X^1$, group $B^2$, and group $X^2$ surrounds group A in a center part of group A. Interaction may become likely to occur between luminescent substances each having such a structure and it becomes possible to further improve the light up-conversion efficiency. Moreover, the two binding hands of group A having such a structure are each positioned on a carbon atom where a radical is likely to be generated when no binding hand exists. That is, in such a structure, the two binding hands of group A inhibit generation of a radical at such a position. This can effectively suppress any decrease in the light up-conversion efficiency due to formation of a dimer resulting from radical reaction between luminescent substances.

[Chemical 8]

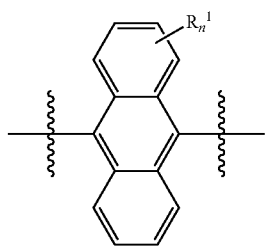
(A1-1)

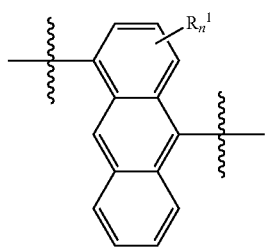
(A1-2)

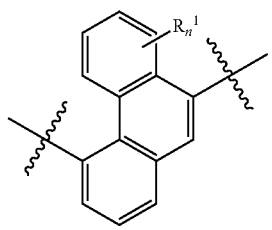
(A2-1)

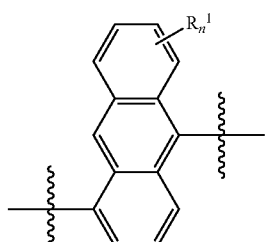
(A3-1)

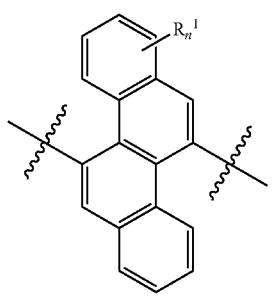
(A4-1)
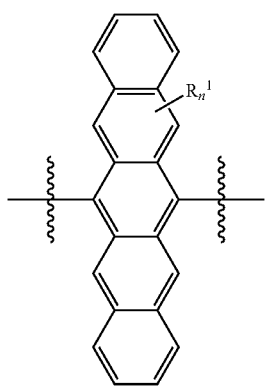
(A5-1)
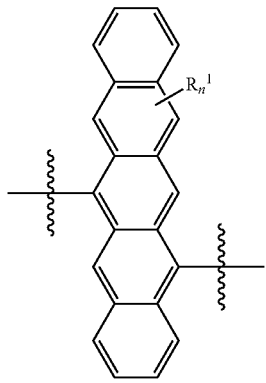
(A5-2)
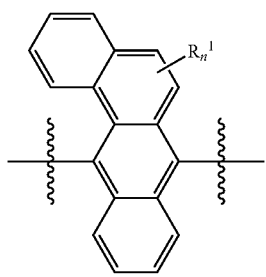
(A6-1)
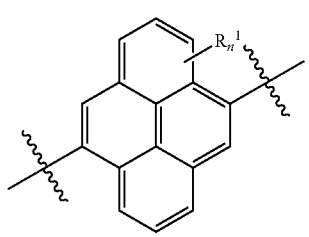
(A9-1)
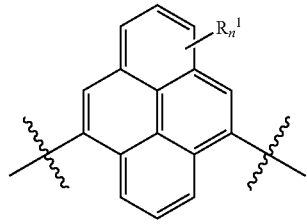
(A9-2)
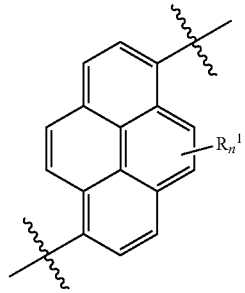
(A9-3)
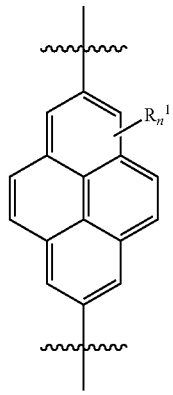
(A9-4)
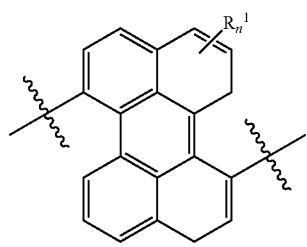
(A14-1)
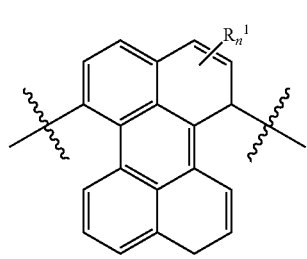
(A14-2)

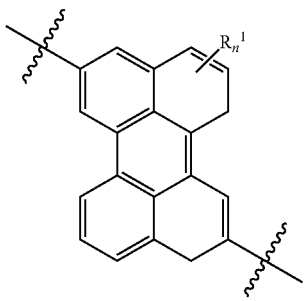

(A14-3)

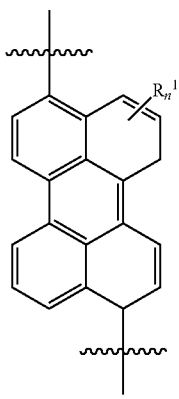

(A14-4)

In each of general formulas (A1-1), (A1-2), (A2-1), (A3-1), (A4-1), (A5-1), (A5-2), (A6-1), (A9-1), (A9-2), (A9-3), (A9-4), (A14-1), (A14-2), (A14-3), and (A14-4), $R_n^1$ is similar to that in each of the above general formulas (A1) to (A23).

In general formula (1), group $B^1$ and group $B^2$ each independently represent a trivalent group represented by the following general formula (2a) or (2b).

[Chemical 9]

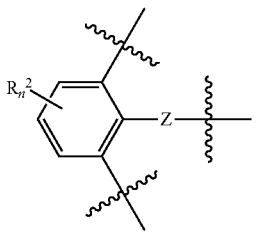

(2a)

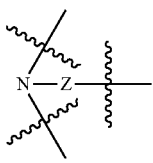

(2b)

In each of general formulas (2a) and (2b), group Z binds to each of the two binding hands of group A. Moreover, the remaining two binding hands in each of general formulas (2a) and (2b) respectively bind to group $X^1$ and group $X^2$ in general formula (1).

In each of general formulas (2a) and (2b), group Z represents a single bond, or a saturated or unsaturated, straight-chain or branched-chain alkylene group. Moreover, in general formula (2a), $R_n^2$ is 0 to 3 substituents which each substitute for a hydrogen atom on a benzene ring and each independently represent an alkyl group, an alkoxy group, a phenyl group, a hydroxyl group, or an amino group. When $R_n^2$ is an alkyl group or an alkoxy group, the carbon number is not particularly limited, but from the view point of reducing the steric hindrance of group $B^1$ and group $B^2$ and facilitating interaction between luminescent substances, the carbon number preferably includes about 1 to 4.

Specific examples of group $B^1$ and group $B^2$ each independently include trivalent groups represented by the following general formulas (3a-1) to (3a-4).

[Chemical 10]

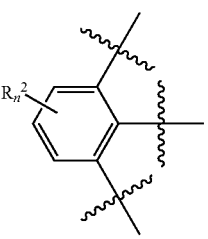

(3a-1)

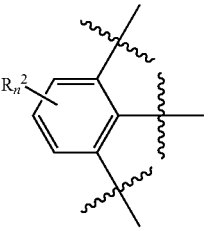

(3a-2)

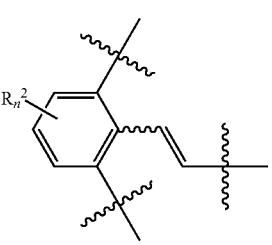

(3a-3)

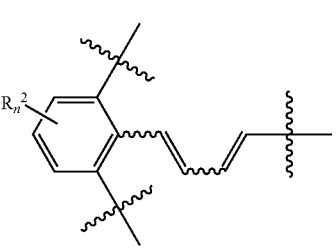

(3a-4)

$R_n^2$ in each of general formulas (3a-1) to (3a-4) is the same as $R_n^2$ in each of the above general formulas (2a) and (2b).

In general formula (1), one of bivalent binding hands of each of group $X^1$ and group $X^2$ binds to group $B^1$, and the other binding hand binds to group $B^2$. Group $X^1$ and group $X^2$ are each independently a straight-chain or branched-chain alkylene group with a carbon number of two or more, optionally having at least one bond selected from the group consisting of an ether bond, an ester bond, an amide bond, and a sulfide bond. From the view point of reducing the steric hindrance of group $X^1$ and group $X^2$ and facilitating interaction between luminescent substances, group $X^1$ and group $X^2$ each include preferably a straight-chain alkylene group with a carbon number of 5 to 10, optionally having at least one bond selected from the group consisting of an ether bond, an ester bond, an amide bond and a sulfide bond, more preferably a straight-chain alkylene group with a carbon number of 5 to 10 or a straight-chain alkylene group with a carbon number of 5 to 10 having an ether bond.

Specific examples of the compound represented by general formula (1) include compounds represented by the following formulas (1a), (1b), and (1c).

and 2,6-dimethyloxyphenyl lithium are reacted to obtain a compound represented by formula (1a2). Next, the compound is dehydrated to obtain 9,10-bis(2,6-dimethoxyphenyl)anthracene (1a3). Dehydration can be conducted, for example, by heating to about 120° C. in the presence of NaI, $NaH_2PO_2.H_2O$, and AcOH. Next, 9,10-bis(2,6-dimethoxyphenyl)anthracene (1a3) is demethylated by using $BBr_3$ to obtain a compound represented by formula (1a4). Finally, the compound of formula (1a4) is reacted with 1,7-dibromoheptane to obtain the compound of formula (1a).

[Chemical 11]

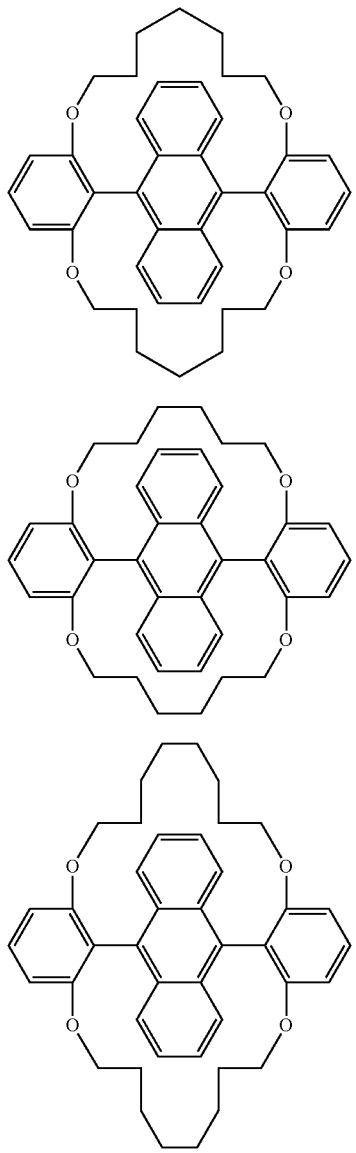

A method of producing the compound represented by general formula (1) is not particularly limited, and the compound can be produced by a known synthesis method. The method of producing the compound represented by general formula (1) will be described using the compound represented by the above formula (1a) as an example. As shown in the following scheme 1, first anthraquinone (1a1)

Scheme 1

[Chemical 12]

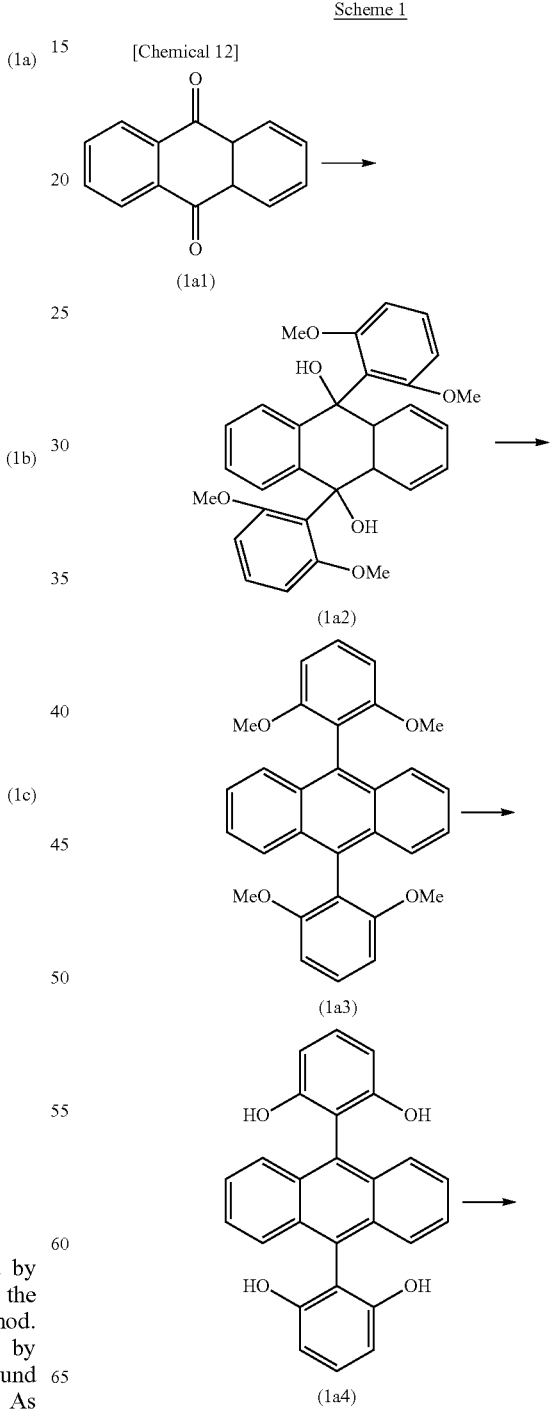

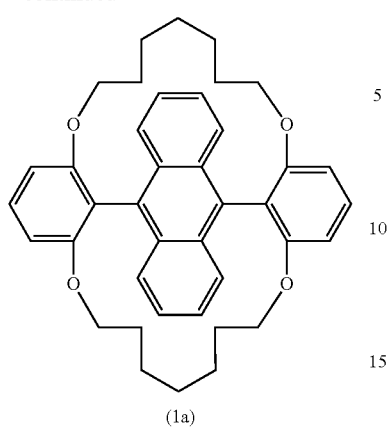

(1a)

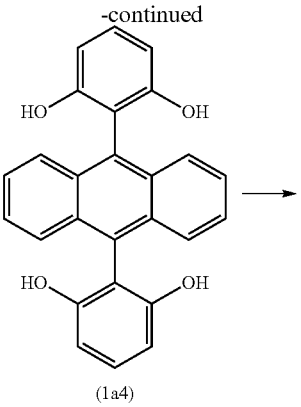

(1a4)

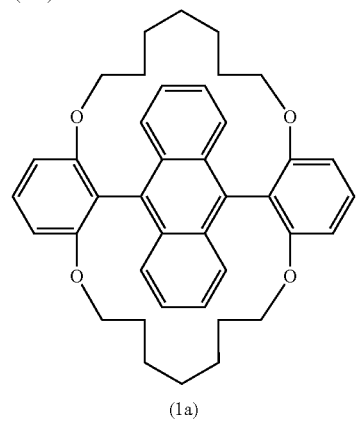

(1a)

Moreover, the compound represented by general formula (1) can also be produced, for example, by a method shown in the following scheme 2. The production method will be described using the compound represented by formula (1a) as an example. First, 9,10-dibromoanthracene (1a5) and 2,6-dimethoxyphenylboronic acid bind to each other by Suzuki-Miyaura coupling reaction to obtain 9,10-bis(2,6-dimethoxyphenyl)anthracene (1a3). Subsequently, in the same manner as the above-described scheme 1, the compound of formula (1a) is obtained.

Scheme 2

[Chemical 13]

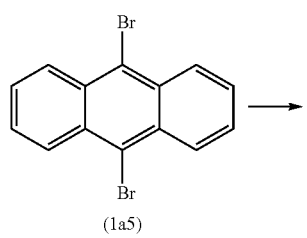

(1a5)

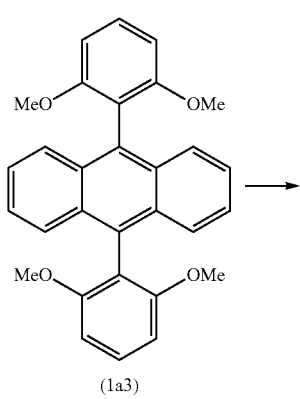

(1a3)

In the later-described light up-conversion material, the light up-conversion luminescent substance of the present invention may be used alone or in a combination of two or more kinds of light up-conversion luminescent substances. Moreover, the content of the light up-conversion luminescent substance of the present invention in the light up-conversion material can be set appropriately, for example, according to application of the light up-conversion material, and typically includes about 1 µM to 10 mM, preferably about 100 µM to 5 mM, more preferably about 1 to 3 mM.

Light Up-conversion Material

The light up-conversion material of the present invention typically contains a photosensitizer in addition to the light up-conversion luminescent substance represented by the above general formula (1). The photosensitizer is not particularly limited as far as it can absorb light energy and transfer the light energy to the light up-conversion luminescent substance of the present invention, and a known photosensitizer can be used. From the viewpoint of desirably transferring light energy to the light up-conversion luminescent substance of the present invention, an example of the photosensitizer preferably includes an organic metal complex. The metal of the organic metal complex is not particularly limited, but examples of the metal include Li, Mg, Al, Ti, V, Mn, Fe, Co, Ni, Cu, Zn, Ga, Ru, Pd, Ag, Re, Os, Ir, Pt, and Pb, and preferably include Pt, and Pd. Specific examples of the organic metal complex include a metal complex of porphyrin or its substitution product, and a metal complex of phthalocyanine or its substitution product, and among them preferably the metal complex of porphyrin or its substitution product.

Preferred examples of the photosensitizer may include a palladium complex of porphyrin or its substitution product, and a platinum complex of porphyrin or its substitution product. Specific examples of the palladium complex of porphyrin or its substitution product include palladium tetrabenzoporphyrin, palladium tetraphenyltetrabenzoporphyrin, palladium octaethylporphyrin, and palladium cyclohexenoporphyrin. Moreover, specific examples of the platinum complex of porphyrin or its substitution product include platinum tetrabenzoporphyrin, platinum tetraphenyltetrabenzoporphyrin, platinum octaethylporphyrin, and platinum cyclohexenoporphyrin.

In the light up-conversion material of the present invention, the photosensitizer may be used alone or in a combination of two or more kinds of photosensitizers.

When the light up-conversion material of the present invention contains the photosensitizer, the content of the photosensitizer can be set appropriately, and typically includes the concentration of about 1/10 to 1/10,000, preferably about 1/10 to 1/500, more preferably 1/50 to 1/200 of the concentration of the light up-conversion luminescent substance.

The light up-conversion material of the present invention typically has a form in which the light up-conversion luminescent substance and the above-described photosensitizer are dispersed in a medium. For example, the above-described amounts of the light up-conversion luminescent substance and the photosensitizer can be dispersed in the medium to prepare the light up-conversion material of the present invention. The medium is not particularly limited, and can be set appropriately according to application of the light up-conversion material of the present invention. Examples of the medium include a solvent, a resin, and a glass.

The medium solvent is not particularly limite, and can be set appropriately according to application of the light up-conversion material. For example, an organic solvent, water, etc., can be used. Specific examples of the organic solvents include nitrile solvents such as acetonitrile and benzonitrile; halogen solvents such as chloroform, dichloromethane, 1,2-dichloroethane, 1,1,2-trichloroethane, chlorobenzene, and o-dichlorobenzene; ether solvents such as tetrahydrofuran and dioxane; aromatic hydrocarbon solvents such as benzene, toluene and xylene; aliphatic hydrocarbon solvents such as cyclohexane, methylcyclohexane, n-pentane, n-hexane, n-heptane, n-octane, n-nonane, and n-decane; ketone solvents such as acetone, methyl ethyl ketone, and cylohexanone; ester solvents such as ethyl acetate, butyl acetate, and ethyl cellosolve acetate; polyols such as ethylene glycol, ethylene glycol monobutyl ether, ethylene glycol monoethyl ether, ethylene glycol monomethyl ether, dimethoxy ethane, propylene glycol, diethoxy methane, triethylene glycol monoethyl ether, glycerin, and 1,2-hexanediol, and derivatives thereof; alcoholic solvents such as methanol, ethanol, propanol, isopropanol, and cyclohexanol; sulfoxide solvents such as dimethyl sulfoxide; and amide solvents such as N-methyl-2-pyrrolidone, and N,N-dimethylformamide, and among them preferably include dimethyl sulfoxide, toluene, tetrahydrofuran, chloroform, dichloromethane, and benzene.

Further, the resin is not particularly limited, and can be selected appropriately according to application of the light up-conversion material. For example, known resins such as a (meth)acryl resin, a polyester resin, a polyurethane resin, an epoxy resin, a polyolefin resin, a polyamide resin, a polystyrene resin, a cellulose resin, an imide resin, a polyvinyl chloride resin, a fluoric resin, a silicone resin, a polycarbonate resin, a polysulfone resin, a cyclic polyolefin resin, a polylactic acid resin, and a vinyl ester resin can be used. The shape of the resin is not particularly limited, and can be selected, for example, according to application of the light up-conversion material. Examples of the shape include a film-like shape, a sheet-like shape, and a fibrous shape.

The glass medium is not particularly limited, and can be selected according to application of the light up-conversion material. For example, quartz glass, borosilicate glass, soda glass, alumina silicate glass, soda lime glass, alkalifree glass and the like, can be used. The shape of the glass is not particularly limited, and can be selected, for example, according to application of the light up-conversion material. Examples of the shape include a film-like shape, a sheet-like shape, and a fibrous shape.

In the light up-conversion material a wavelength of light to be absorbed is typically about 480 to 560 nm, and preferably has peaks of absorption intensity at the positions ranging from about 490 to 510 nm, and about 525 to 540 nm. In the light up-conversion material, a wavelength of light to be emitted is typically about 400 to 550 nm, and preferably has a peak of emission intensity at the positions ranging from about 400 to 480 nm. Moreover, light irradiation power (mW) of light with which the light up-conversion material is irradiated can be selected according to application of the light up-conversion material, and an example of the light irradiation power includes about 0.01 to 10 mW.

Since the light up-conversion material can efficiently convert a wavelength incident to the light up-conversion material into a short wavelength, the light up-conversion material can be used for various applications including solar cells such as organic solar cells, natural light illumination, LEDs, organic EL devices, biomarkers, displays, printing, security recognition, optical data storage units, and sensors. The light up-conversion material can also be used as a method of converting a light wavelength, including irradiating the light up-conversion material with light to cause the emission of light having a shorter wavelength than the radiating light.

EXAMPLES

Hereinafter, the present invention will be described in detail by way of Examples and Comparative Examples. However, the present invention is not limited to these Examples.

Example 1

A compound (sDPA) represented by the following general formula (1a) as a luminescent substance and Pt-octaethylporphyrin (PtOEP) represented by the following formula (4) as a photosensitizer were added into a medium formed of dimethylsulfoxide (DMSO) to prepare a light up-conversion material. The concentration of the luminescent substance in the light up-conversion material was 214 µM, and the concentration of the photosensitizer was 2.2 µM. Note that gas exchange was conducted by using high-purity argon gas (>99.9%) to remove dissolved oxygen in the prepared light up-conversion material.

Next, after the obtained light up-conversion material was irradiated with LED light having a center wavelength of 518 nm, a spectral band width of 40 nm, and light irradiation power of 1 mW, light having a wavelength shown in FIG. 1 was emitted from the light up-conversion material. It was found from FIG. 1 that light having a shorter wavelength (400 to 500 nm) than the wavelength of the incident light (center wavelength 518 nm) is emitted from the light up-conversion material.

[Chemical 14]

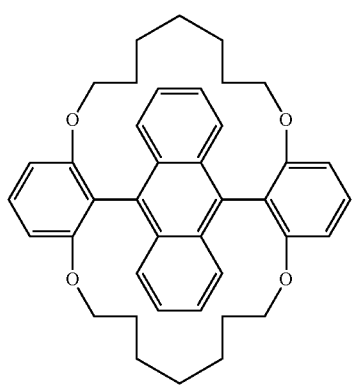

(1a)

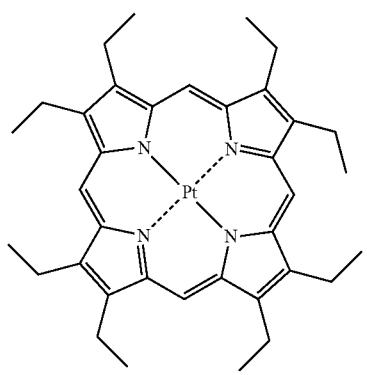

(4)

Next, the light up-conversion material obtained in Example 1 was irradiated with the above-described LED light having light irradiation power varied stepwise in the range from 0.1 mW to 1.3 mW as shown in Table 1, and each emission intensity of the light up-conversion material was measured to determine light up-conversion efficiency. Note that a beam diameter of a light irradiation site was 10 mm. Moreover, the light up-conversion efficiency was determined according to a method described in Tanya N. Singh-Rachford et al., J. Am. Chem. Soc. 2010, 132, 14203-14211.

Specifically, the up-conversion efficiency (φuc) was determined according to the following formula:

$$\Phi uc=2\times\Phi std\times(Astd/Auc)\times(Iuc/Istd)\times(Nuc/Nstd)^2.$$

Here, Astd and Auc denote absorbances at excitation wavelengths of a standard substance and a test sample for up-conversion, respectively. Moreover, Istd and Iuc denote integrated emission intensities obtained by integrating emission intensities of the standard substance and the test sample for up-conversion, respectively by a wavelength over the entire region of the luminescent substance. In particular, as for the test sample for up-conversion, it is an integrated emission intensity regarding an up-conversion light emitting band having a shorter wavelength than the excited light. Moreover, Nstd and Nuc denote refractive indexes of solvents in emission wavelengths of the standard substance and the test sample for up-conversion, respectively. The light up-conversion efficiency was measured under the same optical arrangement and optical conditions for both of the standard substance and the up-conversion test sample in a solution state in a solvent. As the standard substance, 0.40, which is a value of a solution of rhodamine B in methanol (2 µM) described in Kelly G. Casey and Edward L. Quitevis, J. Phys. Chem. 1988, 92, 6590-6594 was used as Φstd.

Comparative Example 1

A light up-conversion material was prepared in the same manner as in Example 1 except that 9,10-diphenylanthracene (210 µm) was used as a luminescent substance. Moreover, in the same manner as in Example 1, dissolved oxygen in the light up-conversion material was removed. Next, in the same manner as in Example 1, the light up-conversion material was irradiated with the above-described LED light having light irradiation power varied stepwise in the range from 0.1 mW to 1.3 mW as shown in Table 1, and light up-conversion efficiency was determined. The result is shown in Table 1.

TABLE 1

| Light irradiation power [mW] | Up-conversion efficiency (%) | |
| --- | --- | --- |
| | Example 1 | Comparative Example 1 |
| 0.1 | 1.51 | 0.18 |
| 0.2 | 3.62 | 0.54 |
| 0.3 | 5.03 | 0.95 |
| 0.4 | 6.18 | 1.25 |
| 0.5 | 7.24 | 1.50 |
| 0.6 | 7.94 | 1.73 |
| 0.7 | 8.92 | 1.94 |
| 0.8 | 9.77 | 2.06 |
| 0.9 | 10.5 | 2.27 |
| 1.0 | 11.1 | 2.36 |
| 1.1 | 11.7 | 2.54 |
| 1.2 | 12.3 | 2.72 |
| 1.3 | 12.7 | 2.89 |

As shown in Table 1, in every light irradiation power, the light up-conversion material prepared in Example 1 exhibited light up-conversion efficiency that is 4 to 7 times higher than that of the light up-conversion material prepared in Comparative Example 1. Moreover, it was found that the maximum light up-conversion efficiency of the light up-conversion material obtained in Example 1 is about 12%, and the light up-conversion material has high efficiency among organic light up-conversion materials known in the related art.

Example 2

A light up-conversion material was prepared in the same manner as in Example 1 except that the concentration of the luminescent substance was 220 µM. Moreover, in the same manner as in Example 1, dissolved oxygen in the light up-conversion material was removed. Next, the light up-conversion material was irradiated with the same LED light as that in Example 1 except that a beam diameter of a light irradiation site was 1.6 mm and light irradiation power was varied stepwise in the range from 0.03 mW to 0.1 mW as shown in Table 2, and light up-conversion efficiency was determined. The result is shown in Table 2.

Comparative Example 2

A light up-conversion material was prepared in the same manner as in Example 2 except that 9,10-diphenylanthracene (230 µm) was used as a luminescent substance. Moreover, in the same manner as in Example 1, dissolved oxygen in the light up-conversion material was removed. Next, in the same manner as in Example 2, the light up-conversion material was irradiated with the above-described LED light having light irradiation power varied stepwise in the range from 0.03 mW to 0.1 mW as shown in Table 2, and light up-conversion efficiency was determined. The result is shown in Table 2.

TABLE 2

| Light irradiation power [mW] | Up-conversion efficiency (%) | |
| --- | --- | --- |
| | Example 2 | Comparative Example 2 |
| 0.03 | 2.25 | 0.50 |
| 0.04 | 3.45 | 0.93 |
| 0.05 | 4.12 | 1.06 |
| 0.06 | 4.69 | 1.33 |
| 0.07 | 5.15 | 1.49 |
| 0.08 | 5.71 | 1.75 |
| 0.09 | 6.11 | 1.96 |
| 0.10 | 6.35 | 2.14 |

As shown in Table 2, when the light irradiation power ranged from 0.03 mW to 0.1 mW, the light up-conversion material prepared in Example 2 exhibited higher light up-conversion efficiency than the light up-conversion material prepared in Comparative Example 2 in every light irradiation power.

Example 3

A compound (194 μM) represented by the following general formula (1b) as a luminescent substance and Pt-octaethylporphyrin (PtOEP, 2.4 μM) represented by the following formula (4) as a photosensitizer were added to a medium formed of dimethylsulfoxide (DMSO) to prepare a light up-conversion material. Next, dissolved oxygen in the prepared light up-conversion material was removed by a frozen-vacuum deaeration using liquid nitrogen.

[Chemical 15]

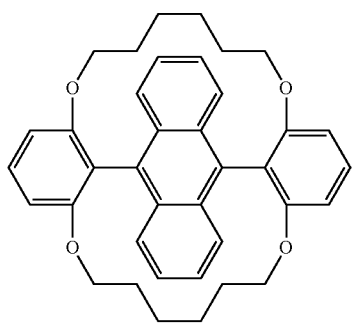

(1b)

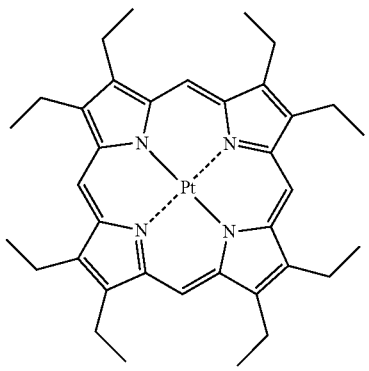

(4)

Figure 2:
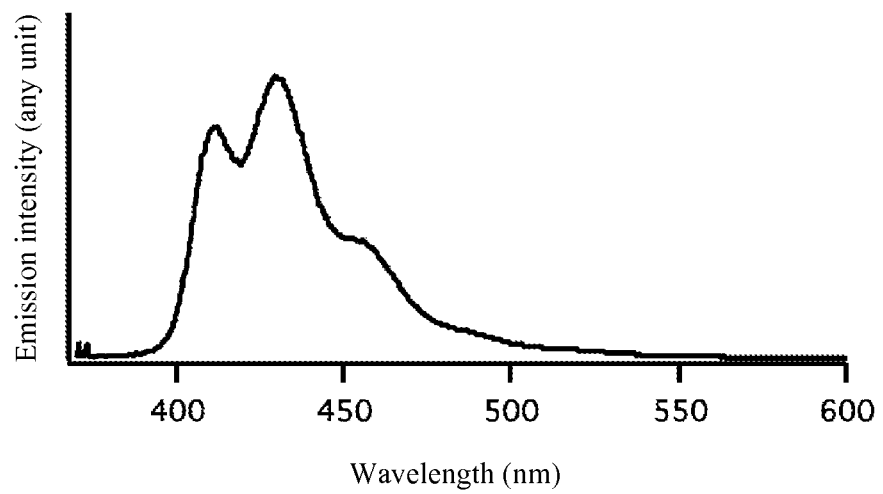
FIG. 2 is a graph showing a relation between a wavelength of emission and an emission intensity by a light up-conversion material obtained in Example 3.

Next, after the light up-conversion material was irradiated with LED light having light irradiation power of 4 mW in the same manner as in Example 1 except that a beam diameter of a light irradiation site was 2.3 mm, light having a wavelength shown in FIG. 2 was emitted from the light up-conversion material. It can be seen from FIG. 2 that light having a shorter wavelength (400 to 500 nm) than the wavelength of the incident light (center wavelength 532 nm) was also emitted from the light up-conversion material using the compound represented by general formula (1b). Light up-conversion efficiency at this time was 12.3%.

Example 4

A light up-conversion material was prepared in the same manner as in Example 3 except that the compound (215 μM) represented by the above general formula (1a) was used as a luminescent substance. Moreover, in the same manner as in Example 3, dissolved oxygen in the light up-conversion material was removed. Next, the light up-conversion material was irradiated with the same LED light as that in Example 3, and light up-conversion efficiency was determined as 15.1%.

Comparative Example 3

A light up-conversion material was prepared in the same manner as in Example 3 except that 9,10-diphenyl anthracene (228 μM) was used as a luminescent substance. Moreover, in the same manner as in Example 3, dissolved oxygen in the light up-conversion material was removed. Next, the light up-conversion material was irradiated with the same LED light as that in Example 3, and light up-conversion efficiency was determined as 7.9%.

As described above, at the light irradiation power of 4 mW, the light up-conversion materials prepared in Example 3 and Example 4 exhibited higher light up-conversion efficiency than the light up-conversion material prepared in Comparative Example 3.

What is claimed is:

1. A light up-conversion material comprising the light up-conversion luminescent substance and a photosensitizer:
wherein the light up-conversion luminescent substance comprises a compound corresponding to the following general formula (1):

[Formula 1]
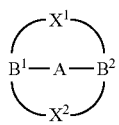
(1)
wherein group A of general formula (1) is any one of polycyclic aromatic compound moieties corresponds to the following general formulas (A1-1), (A1-2), (A2-1), (A3-1), (A4-1), (A5-1), (A5-2), (A6-1), (A9-1), (A9-2), (A9-3), (A9-4), (A14-1), (A14-2), (A14-3), and (A14-4)
[Formula 4]
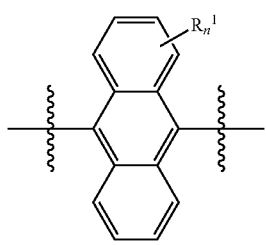
(A1-1)
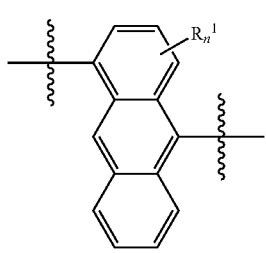
(A1-2)
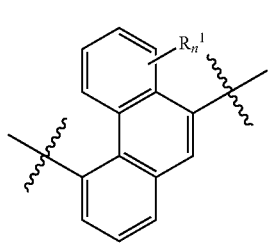
(A2-1)
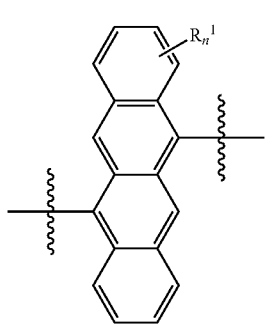
(A3-1)
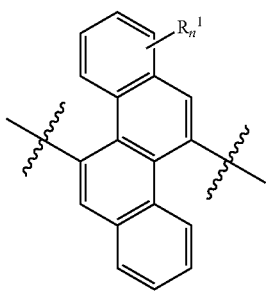
(A4-1)
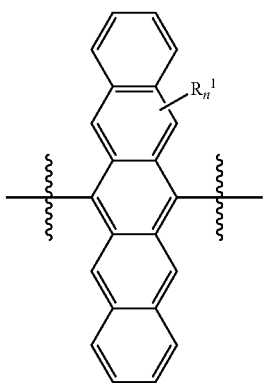
(A5-1)
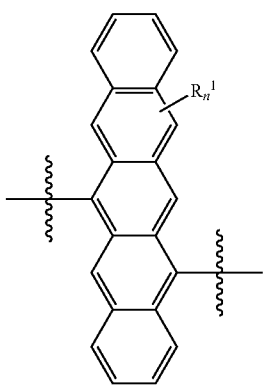
(A5-2)
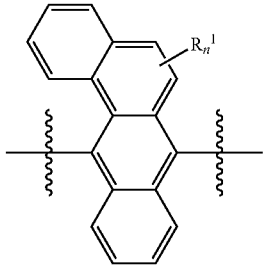
(A6-1)
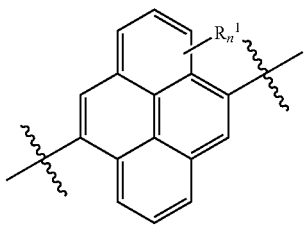
(A9-1)

-continued (A9-2) 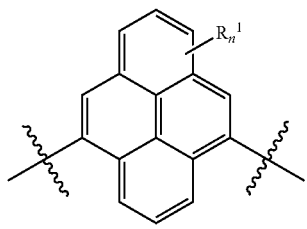

(A9-3) 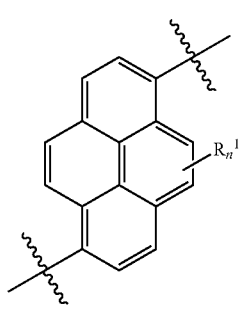

(A9-4) 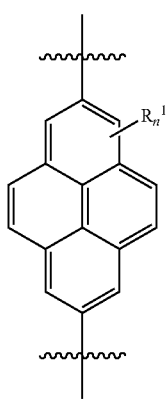

(A14-1) 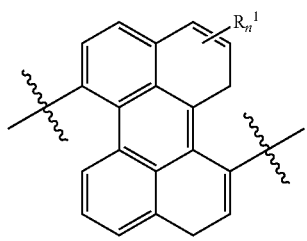

(A14-2) 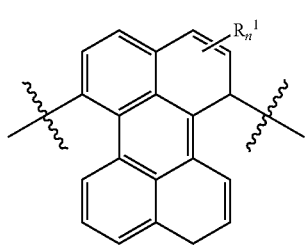

-continued (A14-3) 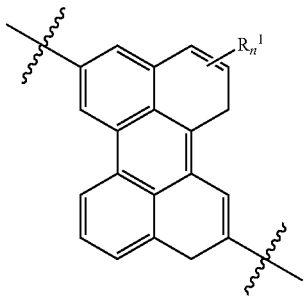

(A14-4) 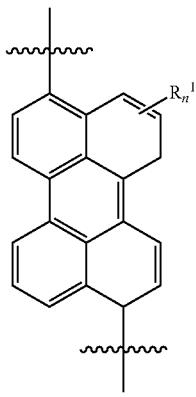

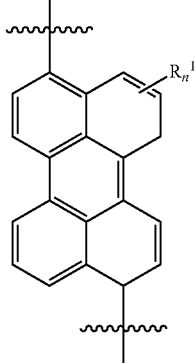

wherein $Rn^1$ is 0 or more substituents wherein each substitute for a hydrogen atom bond to an aromatic ring and each independently corresponds to an alkyl group, an alkoxy group, a phenyl group, a hydroxyl group, or an amino group;

Group $B^1$ and group $B^2$ each independently corresponds to a trivalent group corresponding to the following general formula (2a):

[Formula 2]

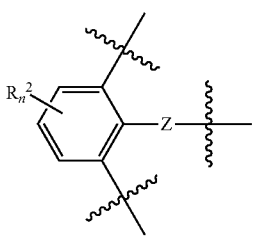

(2a)

wherein general formula (2a), group Z binds to group A, remaining two binding hands bind to group $X^1$ and group $X^2$, and group Z corresponds to a single bond;

$Rn^2$ is 0 to 3 substituents which substitute for a hydrogen atom on a benzene ring and each independently corresponds to an alkyl group, an alkoxy group, a phenyl group, a hydroxyl group, or an amino group; and Group $X^1$ and group $X^2$ each independently corresponds to a straight-chain or branched-chain alkylene group with a carbon number of 5 to 10 having an ether bond.

2. The light up-conversion material according to claim 1, further comprising a solvent, a resin, or a glass.

3. A method of converting a light wavelength, comprising irradiating the light up-conversion material according to claim 1 with light to cause emission of light having a shorter wavelength than the radiating light.

\* \* \* \* \*